(12) United States Patent
Paul

(10) Patent No.: US 9,431,161 B2
(45) Date of Patent: Aug. 30, 2016

(54) MAGNETIC ASSEMBLY HAVING INNER AND OUTER MAGNETS FOR THERAPEUTIC PURPOSES

(71) Applicant: Markland Paul, Salcombe (GB)

(72) Inventor: Markland Paul, Salcombe (GB)

(73) Assignee: BIOFLOW LIMITED, Plymouth (GB)

( * ) Notice: Subject to any disclaimer, the term of this patent is extended or adjusted under 35 U.S.C. 154(b) by 32 days.

(21) Appl. No.: 14/120,811

(22) Filed: Jul. 1, 2014

(65) Prior Publication Data
US 2015/0008999 A1    Jan. 8, 2015

(30) Foreign Application Priority Data

Jul. 3, 2013 (GB) .................................. 1311956.5

(51) Int. Cl.
| | |
|---|---|
| *H01F 1/00* | (2006.01) |
| *H01F 3/00* | (2006.01) |
| *H01F 7/00* | (2006.01) |
| *H01F 7/02* | (2006.01) |
| *A61N 2/00* | (2006.01) |
| *A61N 2/06* | (2006.01) |

(52) U.S. Cl.
CPC ............. *H01F 7/0294* (2013.01); *A61N 2/008* (2013.01); *A61N 2/06* (2013.01)

(58) Field of Classification Search
CPC ....... H01F 7/0294; A61N 2/06; A61N 2/008
USPC ............. 335/296, 302–306, 285; 223/109 A; 292/251.5; 269/8; 24/3.2, 303
See application file for complete search history.

(56) References Cited

U.S. PATENT DOCUMENTS

| | | | | |
|---|---|---|---|---|
| 3,223,898 | A * | 12/1965 | Bey ............................... | 335/295 |
| 3,899,762 | A * | 8/1975 | Studders ....................... | 335/302 |
| 5,196,818 | A * | 3/1993 | Anderson ..................... | 335/285 |
| 5,201,444 | A * | 4/1993 | Simonet ........................ | 224/183 |
| 5,333,767 | A * | 8/1994 | Anderson ..................... | 224/183 |
| 5,611,120 | A * | 3/1997 | Riceman .............. | H01F 7/0263 24/303 |
| 5,813,971 | A * | 9/1998 | Broderick ....................... | 600/15 |
| 6,245,006 | B1 * | 6/2001 | Olson ............................ | 600/15 |
| 6,632,168 | B2 * | 10/2003 | Roberts et al. .................. | 600/9 |
| 6,707,360 | B2 * | 3/2004 | Underwood et al. ......... | 335/288 |
| 7,310,035 | B2 * | 12/2007 | Wooten ......................... | 335/306 |
| 8,727,189 | B2 * | 5/2014 | Zieman et al. ........... | 223/109 A |

FOREIGN PATENT DOCUMENTS

| | | |
|---|---|---|
| DE | 94 13 430.8 | 2/1995 |
| EP | 0 898 982 B1 | 9/2004 |

* cited by examiner

*Primary Examiner* — Bernard Rojas
(74) *Attorney, Agent, or Firm* — Ira S. Dorman

(57) ABSTRACT

A magnetic assembly includes a cylindrical magnet 1 having opposing magnetic poles disposed at respective first and second faces 2 and 3. A cup-shaped ferrous metal housing 4 forms a magnetic shield around the magnet 1 enclosing the second face 3, with an end face 7 continuously surrounding the first face 2. A ring magnet 8 surrounds the housing 4 with opposing magnetic poles disposed at respective first and second faces 9 and 10 with the first face 9 surrounding the end face 7 of the housing. The ring magnet 8 is enclosed within a further ferrous metal housing 11 forming a magnetic shield around the ring magnet and enclosing the second face 10. The further housing 11 has an end face 14 which continuously surrounds the first face 9 of the ring magnet. The end faces of the housings 4 and 11 are proximate to the respective first faces of the magnet 1 and the ring magnet 8 such that these faces together form a planar magnetically active surface.

8 Claims, 2 Drawing Sheets

MAGNETIC ASSEMBLY HAVING INNER AND OUTER MAGNETS FOR THERAPEUTIC PURPOSES

TECHNICAL FIELD OF THE INVENTION

This invention relates to a magnetic assembly for applying a magnetic field to a subject, and in particular a magnetic assembly for applying a magnetic field for therapeutic purposes such as pain relief or conditioning of the blood.

BACKGROUND

Magnetic fields have been applied to the human and animal body for various therapeutic purposes for many years. Localised magnetic fields of suitable intensity can alleviate acute and chronic pain by suppressing neuron action potentials. Various disease states associated with enzyme receptor or ion channel malfunctions may also be relieved by magnotherapy.

EP 0 898 982 B1 claims a magnotherapy device employing fixed magnets which may be placed against the surface of the body so that blood flowing near the surface of the body is subject to changes in magnetic field polarity irrespective of the direction in which blood travels across a magnetically active surface of the device. In this known device a circular magnet is housed within a cup-shaped ferrous metal shield having a circular base wall in contact with one pole of the magnet and a side wall which substantially surrounds the magnet with a gap between the magnet and the side wall. The gap may be air-filled or contain a plastic annulus.

DE 94 13 430 U1 discloses another magnotherapy device having a magnetic core enclosed within a metal housing, with a ring magnet cemented to a closed end of the housing.

Whilst known devices are capable of achieving strong localised changes in the polarity of the magnetic field there is a practical limit to the efficacy which can be achieved since this is determined by the strength of the magnets which are currently available and their physical size.

The present invention seeks to provide a new and inventive form of magnotherapy device which is capable of achieving a more effective magnetic field distribution within an assembly of the same size.

SUMMARY OF THE INVENTION

The present invention proposes a magnetic assembly for applying a magnetic field to a subject, in which the assembly includes:
- an inner magnetic body (1) having opposing magnetic poles disposed at respective first and second faces thereof (2, 3);
- a housing (4) of ferrous metal which forms a magnetic shield around the inner magnetic body enclosing the second face thereof (3) and having an end face (7) continuously surrounding the first face (2) of the inner magnetic body;

characterised by
- a ring magnet (8) which surrounds the housing (4) with opposing magnetic poles disposed at respective first and second faces (9, 10) thereof with the first face (9) surrounding the end face (7) of the housing;

the arrangement being such that the end face (7) of the housing (4) is proximate to the respective first faces (2, 9) of the inner magnetic body (1) and the ring magnet (8) such that said faces together form a magnetically active surface of the assembly for placement adjacent to the subject.

The invention also provides a magnetic assembly in which a ring magnet is enclosed within a housing of ferrous metal which forms a magnetic shield around the ring magnet enclosing a second face thereof and having an end face continuously surrounding a first face of the ring magnet.

The invention also provides a magnetic assembly in which an end face of a housing of ferrous metal is proximate to a first face of a ring magnet and forms part of a magnetically active surface of the assembly.

The invention also provides a magnetic assembly in which a housing of ferrous metal has a base wall closely opposed to a second face of an inner magnetic body.

The invention also provides a magnetic assembly in which a housing of ferrous metal has a base wall closely opposed to a second face of a ring magnet.

The invention also provides a magnetic assembly in which the base walls of a first housing and a second housing are closely opposed to each other.

The invention also provides a magnetic assembly having a magnetically active surface which is substantially planar.

The invention also provides a magnetic assembly incorporated in a bracelet which can be worn on the wrist with a magnetically active surface adjacent to the skin.

BRIEF DESCRIPTION OF THE DRAWINGS

The following description and the accompanying drawings referred to therein are included by way of non-limiting example in order to illustrate how the invention may be put into practice. In the drawings.

DETAILED DESCRIPTION OF THE DRAWINGS

Figure 1:
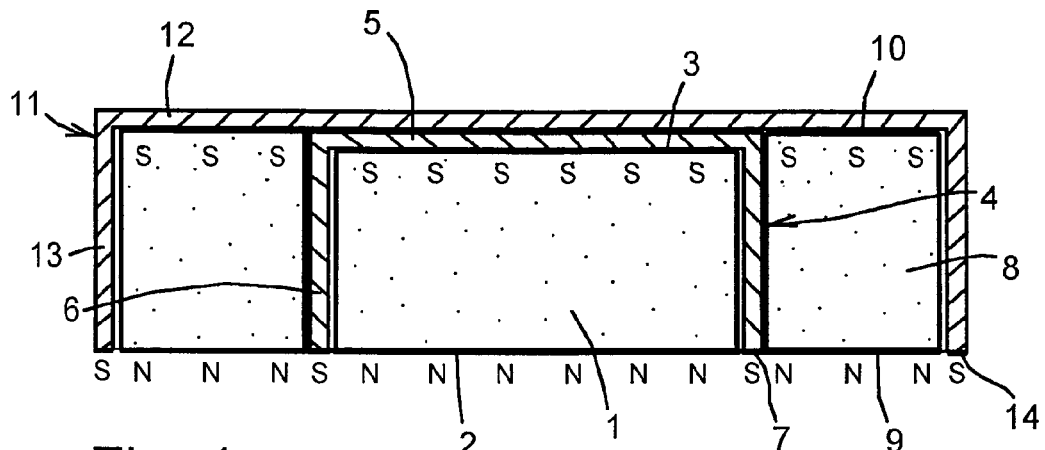
FIG. 1 is an axial section through a magnetic assembly in accordance with the invention.
Figure 2:
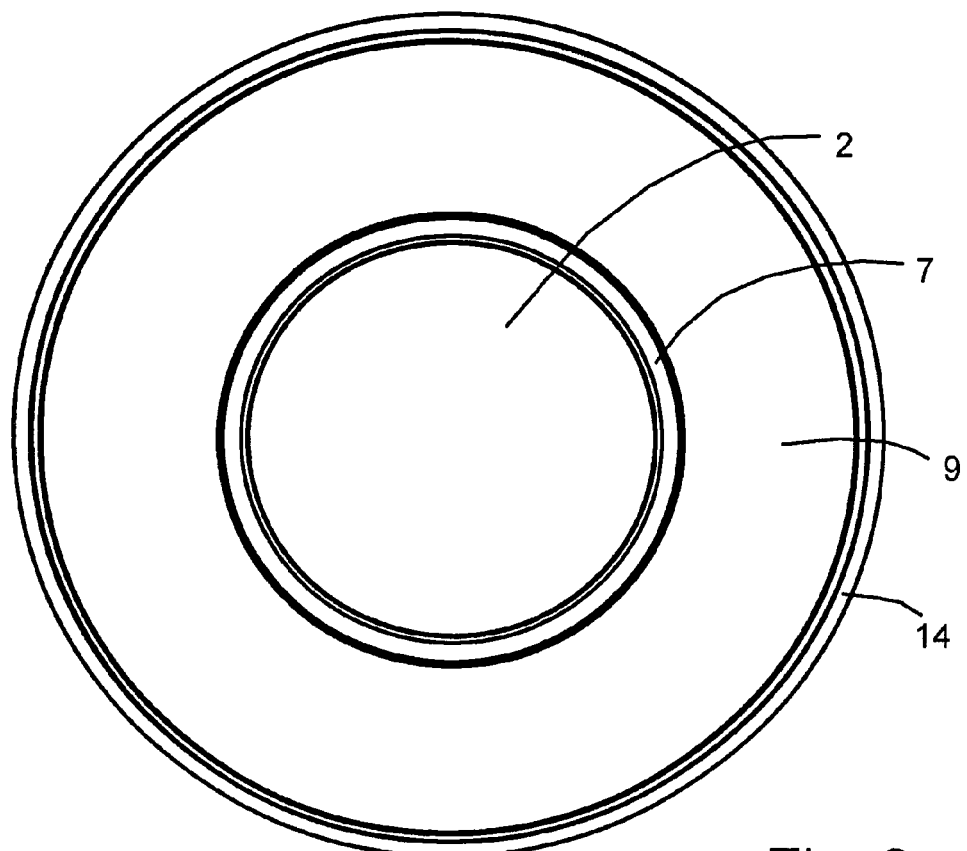
FIG. 2 is an end view showing the magnetically active surface of the magnetic assembly.

Referring firstly to FIGS. 1 and 2, the magnotherapy device comprises an inner short cylindrical magnet 1 having opposite north and south poles (N and S) disposed at flat first and second end faces 2 and 3 respectively. The magnet is housed within a cup-shaped ferrous metal housing 4, which includes a circular base wall 5 surrounded by a cylindrical side wall 6. The housing may be formed by a pressing operation, for example. The outer diameter of the magnet 1 may be slightly less than the inner diameter of the side wall 6 leaving a substantially uniform gap between the magnet and the side wall, typically between 0.1 mm and 2 mm. The housing 4 forms a magnetic shield around the magnet 1 enclosing the second end face 3. The opposed faces of the magnet 1 and the base wall 5 are true and flat so that magnetic attraction causes the second end face 3 of the magnet to be pulled strongly against the base wall. The free end face 7 of the side wall 6 continuously surrounds the first face 2 of the magnet 1 and, in this embodiment, end face 7 is substantially co-planar with the first end face 2 of the magnet 1.

A ring magnet 8 surrounds the side wall 6 of the housing 4 with opposing magnetic poles, N and S, disposed at respective flat first and second faces 9 and 10. The first face 9 with magnetic pole N continuously surrounds the end face 7 of the housing, with or without a small intervening gap. Again, end face 7 is substantially co-planar with the first end face 9 of the ring magnet 8.

The ring magnet 8 is contained within a cup-shaped ferrous metal outer housing 11, which includes a circular base wall 12 surrounded by a cylindrical side wall 13. The housing may be formed by a pressing operation. The outer diameter of the ring magnet 8 may be slightly less than the inner diameter of the side wall 13 leaving a substantially uniform gap between the magnet and the side wall, typically between 0.1 mm and 2 mm. The outer housing 11 forms a magnetic shield around the ring magnet 8 enclosing the second end face 10. The opposed faces of the ring magnet 8 and the base wall 12 are true and flat so that magnetic attraction causes the second end face 10 of the magnet to be pulled strongly against the base wall 12. A central region of the base wall 12 is opposed to the base wall 5 of the inner housing, but the amount of repulsion between the like poles S and S is small due to the fact that the lines of magnetic flux are largely confined within the housings 4 and 11. If desired, however, the base wall 12 may be of annular form with a central aperture. The free end face 14 of the side wall 13 continuously surrounds the first face 9 of the ring magnet 8 and, again, end face 14 is substantially co-planar with the first end face 9 of the ring magnet.

The lines of magnetic flux from the second end face 3 of the inner magnet 1 are directed through the inner shield 4 forming an opposite magnetic pole at the end face 7 which substantially surrounds the exposed first face 2 of the inner magnet. A highly concentrated field strength is thus created in this region. Moreover, the end face 7 of the inner housing is surrounded by an opposite magnetic pole at the first end face 9 of the ring magnet 8, providing a further concentration in field strength. This is further magnified by an opposing magnetic pole surrounding the end face 9 due to the lines of magnetic flux from the end face 10 being directed through the outer housing 11 to the end face 14.

It will thus be appreciated that the proximate end faces 2, 7, 9 and 14 of the magnets 1, 8 and their respective housings 4 and 11 provide a highly concentrated magnetic flux produced by the adjacent magnetic poles, and these faces together form a planar magnetically active surface of the assembly for placement adjacent to a subject. Thus, blood flowing through the subject's skin in a direction which is substantially parallel to the magnetically active surface is successively subjected to multiple changes in the magnetic field, S-N-S-N-S-N-S, and such a change in field polarity will occur irrespective of the radial direction in which the blood flows across the magnetically active surface.

If the magnets are inverted the poles will of course be reversed, but the blood will be similarly be subjected to multiple changes in a highly concentrated magnetic field, irrespective of the radial direction of flow.

Although the magnetically active surface of the assembly will usually be substantially planar it could, for example, be of slightly domed or dished shape to maintain close surface proximity to the subject.

Figure 3:
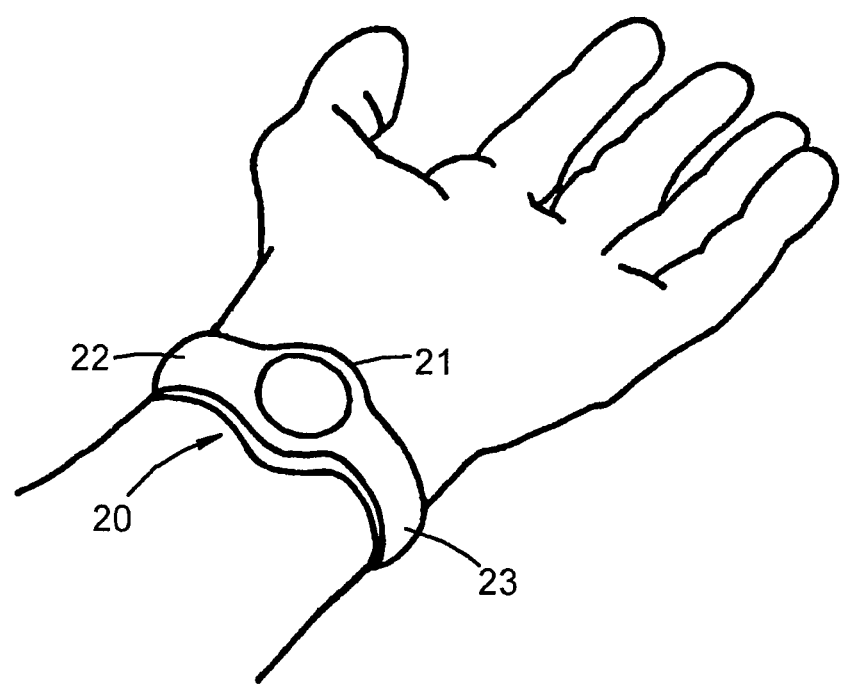
FIG. 3 is a general view of a magnotherapy device containing the magnetic assembly.

As shown in FIG. 3, the magnetic assembly may be mounted within a moulded plastic or other non-ferrous housing 20 which is provided with means for securing the housing to the body of a human or animal subject with a contact surface of the housing positioned against the body. The magnetically active surface of the assembly is either exposed and substantially flush with this contact surface or separated therefrom by a thin non-ferrous wall. The housing 20 may, for example, comprise a hollow circular part 21 which is formed with opposing sections 22 and 23 of a wrist band. The two sections may be mutually securable by a clasp or similar device, but the wrist band could also be in the form of a continuous expandable loop.

In the magnetic assembly of the invention the small annular space formed between the magnets and the side walls of their respective housings may be filled by a tubular spacer provided by an annulus of polyethylene or similar non-ferrous material.

If an even greater variation in magnetic flux is required further ring magnets and housings could be mounted about the outer housing 11 in similar manner.

Whilst the above description places emphasis on the areas which are believed to be new and addresses specific problems which have been identified, it is intended that the features disclosed herein may be used in any combination which is capable of providing a new and useful advance in the art.

The invention claimed is:

1. A magnetic assembly for applying a magnetic field to the body of a human or animal a subject, in which the assembly includes:
    an inner magnetic body (1) having opposing magnetic poles disposed at respective first and second faces (2, 3) of said body (1);
    a housing (4) of ferrous metal which forms a magnetic shield around the inner magnetic body, enclosing the second face (3) thereof, said housing having an end face (7) continuously surrounding the first face (2) of the inner magnetic body; and
    a ring magnet (8) which surrounds the housing (4), said ring magnet having opposing magnetic poles disposed at respective first and second faces (9, 10) of said ring magnet, with the first face (9) of said ring magnet surrounding the end face (7) of the housing;
    the arrangement being such that the end face (7) of the housing (4) is proximate to the respective first faces (2, 9) of the inner magnetic body (1) and the ring magnet (8), such that said first face (2) of the inner magnetic body, said end face (7) of the housing, and said first face of the ring magnet together form a magnetically active surface of the assembly for placement adjacent to the body of a subject.

2. A magnetic assembly according to claim 1 in which the ring magnet (8) is enclosed within a further housing (11) of ferrous metal which forms a magnetic shield around the ring magnet enclosing the second face (10) thereof and having an end face (14) continuously surrounding the first face (9) of the ring magnet.

3. A magnetic assembly according to claim 2 in which the end face (14) of the further housing (11) is proximate to the first face (9) of the ring magnet (8) and forms part of the magnetically active surface of the assembly.

4. A magnetic assembly according to claim 1 in which the housing (4) has a base wall (5) closely opposed to the second face (3) of the inner magnetic body (1).

5. A magnetic assembly according to claim 2 in which the further housing (11) has a base wall (12) closely opposed to the second face (10) of the ring magnet (8).

6. A magnetic assembly according to claim 5 in which the housing (4) has a base wall (5) closely opposed to the second face (3) of the inner magnetic body (1) and the base walls (5, 12) of the ferrous metal housing (4) and the further housing (11) are closely opposed to each other.

7. A magnetic assembly according to claim 1 in which the magnetically active surface is planar.

8. A magnetic assembly according to claim 1 which is incorporated in a bracelet (20) which can be worn on the wrist of a human subject, with the magnetically active surface adjacent to his or her skin.

* * * * *